United States Patent [19]

Chang et al.

[11] 4,298,603

[45] Nov. 3, 1981

[54] O-AMINOALKYLSALICYLATES

[75] Inventors: Ching-Te Chang, Taipei; Tsung-Tsan Su, Hsinchu, both of Taiwan

[73] Assignee: Industrial Technology Research Institute, Taiwan

[21] Appl. No.: 100,891

[22] Filed: Dec. 6, 1979

[51] Int. Cl.³ .................. A61K 31/615; C07C 101/42
[52] U.S. Cl. ..................................... 424/230; 424/231; 424/232; 560/42; 562/451; 544/399; 544/335; 544/224; 546/238; 546/342; 260/239 B; 260/326.41; 548/341; 548/378
[58] Field of Search .................. 560/37, 42; 562/442, 562/451; 424/250, 230, 232, 256, 274; 260/239 B, 326.41; 546/238, 242; 548/341, 378; 544/399, 335, 224

[56] References Cited

PUBLICATIONS

Moore et al., J.A.C.S. 78, 5633–5636, (1956).
Mayr et al., Chem. Absts., 65, 2178(b), 1966.
Wagner et al., Synthetic Organic Chem., John Wiley & Sons, Inc., N.Y., pp. 480–481, 486–487, (1965).
Gringauz, J. Pharm. Sci., 59(3), 422–425, (1970).
Dall'Asta et al., Chem. Absts., 68, 104686(y), 1968.

Primary Examiner—G. T. Breitenstein
Attorney, Agent, or Firm—James J. Long

[57] ABSTRACT

Compounds of the formula

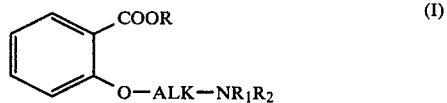

or pharmaceutically acceptable acid addition salts thereof (for example, a chloride) are useful as local anesthetics. In the compound of the formula (I), R is hydrogen or $C_1$–$C_{14}$ alkyl, ALK is $C_1$–$C_4$ alkylene, $R_1$ and $R_2$ may be the same or different and are hydrogen or $C_1$–$C_6$ alkyl or $R_1$ and $R_2$ taken together form a 5 to 7 atom ring which contains 1 to 2 nitrogen atoms.

8 Claims, No Drawings

O-AMINOALKYLSALICYLATES

The present invention relates to novel O-aminoalkylsalicylates useful as local anesthetics and to processes for their preparation.

The compounds of the present invention are compounds of the formula

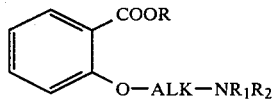 (I)

or pharmaceutically acceptable acid addition salts thereof (for example, a chloride). In the compound of the formula (I), R is hydrogen or $C_1$–$C_{14}$ alkyl, ALK is $C_1$–$C_4$ alkylene, $R_1$ and $R_2$ may be the same or different and are hydrogen or $C_1$–$C_6$ alkyl or $R_1$ and $R_2$ taken together form a 5 to 7 atom ring which contains 1 to 2 nitrogen atoms.

The compounds of the present invention are useful as local anesthetics. Although morpholinoalkyl ethers of salicylic acid had been reported to possess local anesthetic activity (U.S. Pat. No. 2,810,719), it was found that their activity is not as effective as the activity of similar compounds of the present invention. (See Table III and IV of Example 32).

In general, the compounds of the present invention are prepared by forming an alkali (for example, sodium, potassium) or alkaline earth metal (for example, calcium) salt of a salicylate, having the formula

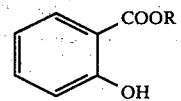 (II)

wherein R is a $C_1$–$C_{14}$ alkyl group and reacting the resultant salt of the salicylate with an aminoalkyl compound of the formula

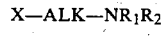

X—ALK—NR$_1$R$_2$ (III)

or its salts, wherein $R_1$ and $R_2$ may be the same or different and are hydrogen or $C_1$–$C_6$ alkyl, or $R_1$ and $R_2$ taken together form a 5 to 7 atom ring which contains 1 to 2 nitrogen atoms, ALK is a $C_1$–$C_4$ alkylene radical, X is a halide (for example, fluoride, chloride, bromide, iodide) or other good leaving group (for example, sulfate, toluenesulfonyl) to produce the corresponding aryl ether of the aminoalkanol. Examples of the 5 to 7 atom rings that may be formed by $R_1$ and $R_2$ taken together are pyrrolidine, piperidine, piperazine and hexamethyleneimine (azacycloheptane).

This etherification not only can be done by using an alkali or alkaline earth metal salt of a salicylate as a starting material, but also can be conducted in the presence of an alkali condensation medium, e.g. alkali alkoxide or alkali carbonate. Examples of suitable alkoxides are those derived from $C_3$–$C_{10}$ alcohols.

The desired compound (I) can also be prepared by introducing an aminoalkyl group first, followed by introducing the desired ester. For example, after introducing an aminoalkyl group, a methyl O-(aminoalkyl) salicylate derivative can be hydrolyzed in the presence of an acid to give an O-aminoalkylsalicylic acid derivative having the formula

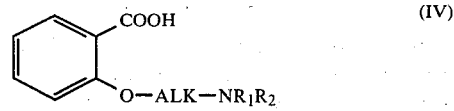 (IV)

wherein $R_1$, $R_2$ and ALK are as defined above, which, in turn, reacts with a compound of the general formula ROH, wherein R is a $C_1$–$C_{14}$ alkyl group, by the use of an acid as the condensation agent.

The desired ester group can also be introduced by catalyzed transesterification. For example, a methyl O-(aminoalkyl) salicylate derivative can be converted into a desired alkyl O-(aminoalkyl) salicylate by reacting the former with an alkyl alcohol in the presence of a catalyst.

The aforementioned reactions are carried out at temperatures in the range of 20°–150° C. Preferably, the etherification is conducted in the presence of an alkali condensing agent, e.g. an alkali alkoxide (for example a sodium or potassium alkoxide), and the condensation is effected in an organic solvent, preferably a $C_3$–$C_{10}$ alcohol, e.g. t-butyl alcohol. Examples of suitable alkoxides are those derived from $C_3$–$C_{10}$ alcohols.

A compound of the present invention can be converted to its corresponding acid addition salt by reacting such a compound with the appropriate acid. For example, reaction with hydrochloric acid will yield the corresponding hydrochloride salt.

The present invention is further described by the following illustrative examples, which are not to be construed in any way as limiting the spirit or scope of the invention. Relative amounts of material are given in parts by weight unless otherwise indicated.

EXAMPLE 1

Methyl O-(3-Dimethylaminopropyl)salicylate

A mixture of 1.52 parts of methyl salicylate and 0.23 parts of Na in 20 ml of t-butyl alcohol is heated at reflux for 30 minutes. To this mixture, 1.50 parts of 3-dimethylaminopropyl chloride is added. The resulting mixture is heated at reflux for 3–7 hours, and then evaporated to remove t-butyl alcohol. The residue thus obtained is transferred into a separatory funnel containing 10 ml of water. The aqueous solution is extracted with ether. The separated ether layer is washed with a second portion of water followed by the extraction with a 20% HCl aqueous solution. The separated acidic aqueous layer is then basicified with 20% NaOH aqueous solution followed by extraction with ether. The ether layer obtained is washed with water and saturated NaCl aqueous solution. After drying over anhydrous MgSO$_4$, the ether is removed under vacuo to give 2.24 parts of methyl O-(3-dimethylaminopropyl)salicylate. Nuclear magnetic resonance spectra of the aforementioned compounds and of the compounds prepared in Examples 2–30, below, were obtained on a Varian A-60A (trademark) spectrophotometer. The results are shown in Table I, following Example 31. Chemical shifts for each compound are given in Delta units (ppm) from the interval standard, TMS. The abbreviation (d), (q), (m), (s), (t), or (hep) after the significant frequency figure stands for doublet, quartet, multiplet, singlet, triplet or heptet, respectively.

EXAMPLE 2

Ethyl O-(2-Dimethylamino-1(and 2)-methylethyl)salicylate

By a process similar to that of Example 1, using 3 parts of ethyl salicylate, 0.83 parts of Na in 8 ml of t-butyl alcohol and 4.28 parts of 2-dimethylaminoisopropyl chloride, ethyl O-(2-dimethylamino-1(and 2)-methylethyl)salicylate is produced. Yield of the product is 3.47 parts.

EXAMPLE 3

Isopropyl O-(3-Dimethylaminopropyl)salicylate

By a process similar to that of Example 1, using 1.82 parts of isopropyl salicylate, 0.23 parts of Na in 10 ml of isopropyl alcohol, and 1.21 parts of 3-dimethylaminopropyl chloride, isopropyl O-(3-dimethylaminopropyl)salicylate is produced. The yield is 0.85 parts.

EXAMPLE 4

Isopropyl O-(3-Dimethylaminopropyl)salicylate

By a process similar to that of Example 1, using 1.52 parts of methyl salicylate, 0.23 parts of Na in 10 ml of isopropyl alcohol, and 1.50 parts of 3-dimethylaminopropyl chloride, isopropyl O-(3-dimethylaminopropyl)salicylate is produced. The yield is 2.14 parts.

EXAMPLE 5 n-Butyl O-(3-Dimethylaminopropyl)salicylate

By a process similar to that of Example 1, using 1.94 parts of n-butyl salicylate, 0.25 parts of Na in 10 ml of n-butyl alcohol, and 1.33 parts of 3-dimethylaminopropyl chloride, n-butyl O-(3-dimethylaminopropyl)salicylate is produced. The yield is 1.35 parts.

EXAMPLE 6 n-Butyl O-(3-Diethylaminopropyl)salicylate

By a process similar to that of Example 1, using 0.99 parts of n-butyl salicylate, 0.23 parts of Na in 20 ml of n-butyl alcohol, and 1.50 parts of 3-diethylaminopropyl chloride, n-butyl O-(3-diethylaminopropyl)salicylate is produced. The yield is 1.05 parts.

EXAMPLE 7 n-Butyl O-(2-Dimethylaminoethyl)salicylate

By a process similar to that of Example 1, using 1.95 parts of n-butyl salicylate, 0.27 parts of Na in 10 ml of n-butyl alcohol, and 1.19 parts of 2-dimethylaminoethyl chloride, n-butyl O-(2-dimethylaminoethyl)salicylate is produced. The yield is 0.96 parts.

EXAMPLE 8 n-Butyl O-(2-Diisopropylaminoethyl)salicylate

By a process similar to that of Example 1, using 1.94 parts of n-butyl salicylate, 0.28 parts of Na in 20 ml of n-butyl alcohol, and 1.82 parts of 2-diisopropylaminoethyl chloride, n-butyl O-(2-diisopropylaminoethyl)salicylate is produced. The yield is 1.94 parts.

EXAMPLE 9 n-Butyl O-(3-Piperidinopropyl)salicylate

By a process similar to that of Example 1, using 1.95 parts of n-butyl salicylate, 0.28 parts of Na in 10 ml of n-butyl alcohol, and 1.78 parts of N-(3-chloropropyl)piperidine, n-butyl O-(3-piperidinopropyl)salicylate is produced. The yield is 1.88 parts.

EXAMPLE 10 n-Butyl O-(3-Dimethylamino-2-methylpropyl)salicylate

By a process similar to that of Example 1, using 1.94 parts of n-butyl salicylate, 0.30 parts of Na in 10 ml of n-butyl alcohol, and 1.50 parts of 3-dimethylamino-2-methylpropyl chloride, n-butyl O-(3-dimethylamino-2-methylpropyl)salicylate is produced. The yield is 1.94 parts.

EXAMPLE 11 n-Butyl O-(2-Morpholinoethyl)salicylate

By a process similar to that of Example 1, using 1.96 parts of n-butyl salicylate, 0.27 parts of Na in 10 ml of n-butyl alcohol, and 1.66 parts of N-2-(chloroethyl)-morpholine, n-butyl O-(2-morpholinoethyl)salicylate is produced. The yield is 1.03 parts.

EXAMPLE 12 n-Butyl O-(2-Piperidinoethyl)salicylate

By a process similar to that of Example 1, using 1.96 parts of n-butyl salicylate, 0.31 parts of Na in 10 ml of n-butyl alcohol, and 1.65 parts of N-(2-chloroethyl)-piperidine, n-butyl O-(2-piperidinoethyl)salicylate is produced. The yield is 1.76 parts.

EXAMPLE 13 n-Butyl O-(2-Dimethylamino-1(and 2)-methylethyl)salicylate

By a process similar to that of Example 1, using 1.96 parts of n-butyl salicylate, 0.27 parts of sodium in 10 ml of n-butyl alcohol, and 1.35 parts of 2-dimethylaminoisopropyl chloride, n-butyl O-(2-dimethylamino-1(and 2)-methylethyl)salicylate is produced. The yield is 1.31 parts.

EXAMPLE 14 n-Butyl O-[2-(Hexamethyleneimine)-ethyl]salicylate

By a process similar to that of Example 1, using 1.95 parts of n-butyl salicylate, 0.28 parts of sodium in 10 ml of n-butyl alcohol, and 1.81 parts of 2-(hexamethyleneimine)-ethyl chloride, n-butyl O-[2-(hexamethyleneimine)-ethyl]salicylate is produced. The yield is 2.06 parts.

EXAMPLE 15 n-Butyl O-(2-Diethylaminoethyl)salicylate

By a process similar to that of Example 1, using 1.94 parts of n-butyl salicylate, 0.28 parts of Na in 10 ml of n-butyl alcohol, and 1.58 parts of 2-diethylaminoethyl chloride, n-butyl O-(2-diethylaminoethyl)salicylate is produced. The yield is 1.64 parts.

EXAMPLE 16 iso-Amyl O-(3-Dimethylaminopropyl)salicylate

By a process similar to that of Example 1, using 2.50 parts of iso-amyl salicylate, 0.55 parts of Na in 20 ml of iso-amyl alcohol, and 2.9 parts of dimethylaminopropyl chloride, iso-amyl O-(3-dimethylaminopropyl)salicylate is produced. The yield is 2.50 parts.

EXAMPLE 17 n-Amyl O-(3-Dimethylaminopropyl)salicylate

By a process similar to that of Example 1, using 2.08 parts of n-amyl salicylate, 0.27 parts of Na in 10 ml of n-amyl alcohol, and 1.33 parts of 3-dimethylaminopropyl chloride, n-amyl O-(3-dimethylaminopropyl)salicylate is produced. The yield is 1.62 parts.

EXAMPLE 18 n-Amyl O-[2-(Hexamethyleneimine)-ethyl]salicylate

By a process similar to that of Example 1, using 2.09 parts of n-amyl salicylate, 0.3 parts of Na in 10 ml of n-amyl alcohol, and 1.84 parts of 2-(hexamethyleneimine)-ethyl chloride, n-amyl O-[2-(hexamethyleneimine)-ethyl]salicylate is produced. The yield is 2.15 parts.

EXAMPLE 19 n-Amyl O-(3-Diethylaminopropyl)salicylate

By a process similar to that of Example 1, using 2.10 parts of n-amyl salicylate, 0.29 parts of Na in 10 ml of n-amyl alcohol, and 1.65 parts of 3-diethylaminopropyl chloride, n-amyl O-(3-diethylaminopropyl)salicylate is produced. The yield is 2.22 parts.

EXAMPLE 20 n-Amyl O-(3-Piperidinopropyl)salicylate

By a process similar to that of Example 1, using 2.08 parts of n-amyl salicylate, 0.28 parts of Na in 10 ml of n-amyl alcohol, and 1.78 parts of N-(3-chloropropyl)-piperidine, n-amyl O-(3-piperidinopropyl)salicylate is produced. The yield is 2.64 parts.

EXAMPLE 21 n-Amyl O-(2-Piperidinoethyl)salicylate

By a process similar to that of Example 1, using 2.09 parts of n-amyl salicylate, 0.28 parts of Na in 10 ml of n-amyl alcohol, and 1.77 parts of N-(2-chloroethyl)-piperidine, n-amyl O-(2-piperidinoethyl)salicylate is produced. The yield is 2.40 parts.

EXAMPLE 22 n-Amyl O-(2-Morpholinoethyl)salicylate

By a process similar to that of Example 1, using 2.10 parts of n-amyl salicylate, 0.28 parts of Na in 10 ml of n-amyl alcohol, and 1.69 parts of N-(2-chloroethyl)-morpholine, n-amyl O-(2-morpholinoethyl)salicylate is produced. The yield is 2.26 parts.

EXAMPLE 23 n-Amyl O-(2-Diisopropylaminoethyl)salicylate

By a process similar to that of Example 1, using 2.09 parts of n-amyl salicylate, 0.27 parts of Na in 10 ml of n-amyl alcohol, and 1.82 parts of 2-diisopropylaminoethyl chloride, n-amyl O-(2-diisopropylaminoethyl)salicylate is produced. The yield is 1.91 parts.

EXAMPLE 24 n-Amyl O-(2-Dimethylamino-1(and 2)-methylethyl)salicylate

By a process similar to that of Example 1, using 2.09 parts of n-amyl salicylate, 0.28 parts of Na in 10 ml of n-amyl alcohol, and 1.36 parts of 2-dimethylaminoisopropyl chloride, n-amyl O-(2-dimethylamino-1(and 2)-methylethyl)salicylate is produced. The yield is 2.29 parts.

EXAMPLE 25 n-Amyl O-(3-Dimethylamino-2-methylpropyl)salicylate

By a process similar to that of Example 1, using 2.09 parts of n-amyl salicylate, 0.28 parts of Na in 10 ml of n-amyl alcohol, and 1.51 parts of 3-dimethylamino-2-methylpropyl chloride, n-amyl O-(3-dimethylamino-2-methylpropyl)salicylate is produced. The yield is 2.14 parts.

EXAMPLE 26 n-Amyl O-(2-Dimethylaminoethyl)salicylate

By a process similar to that of Example 1, using 2.09 parts of n-amyl salicylate, 0.54 parts of Na in 20 ml of n-amyl alcohol, and 1.67 parts of 2-dimethylaminoethyl chloride HCl, n-amyl O-(2-dimethylaminoethyl)salicylate is produced. The yield is 1.87 parts.

EXAMPLE 27 n-Amyl O-(2-Diethylaminoethyl)salicylate

By a process similar to that of Example 1, using 2.09 parts of n-amyl salicylate, 0.30 parts of Na in 10 ml of n-amyl alcohol, and 1.49 parts of 2-diethylaminoethyl chloride, n-amyl O-(2-diethylaminoethyl)salicylate is produced. The yield is 1.68 parts.

EXAMPLE 28 n-Hexyl O-(3-Dimethylaminopropyl)salicylate

By a process similar to that of Example 1, using 2.23 parts of n-hexyl salicylate, 0.28 parts of Na in 10 ml of hexanol, and 1.35 parts of 3-dimethylaminopropyl chloride, n-hexyl O-(3-dimethylaminopropyl)salicylate is produced. The yield is 1.54 parts.

EXAMPLE 29 n-Decyl O-(3-Dimethylaminopropyl)salicylate

By a process similar to that of Example 1, using 2.79 parts of n-decyl salicylate, 0.27 parts of Na in 30 ml of t-butyl alcohol, and 1.42 parts of 3-dimethylaminopropyl chloride, n-decyl O-(3-dimethylaminopropyl)salicylate is produced. The yield is 1.45 parts.

EXAMPLE 30 n-Dodecyl O-(3-Dimethylaminopropyl)salicylate

By a process similar to that of Example 1, using 3.10 parts of n-dodecyl salicylate, 0.28 parts of Na in 30 ml of t-butyl alcohol, and 1.16 parts of 3-dimethylaminopropyl chloride, n-dodecyl O-(3-dimethylaminopropyl)salicylate is produced. The yield is 1.58 parts.

EXAMPLE 31 n-Butyl O-(3-Dimethylaminopropyl)salicylate

A mixture of 0.51 parts of isopropyl O-(3-dimethylaminopropyl)salicylate and 0.06 parts of Na in 2 ml of n-butyl alcohol is stirred at room temperature for 3 hours. The resulting mixture is evaporated at vacuo to remove n-butyl alcohol. The residue thus obtained is partitioned between ether and water. The separated ether layer is washed with water and saturated NaCl aqueous solution. After drying over anhydrous $MgSO_4$, the ether is removed at vacuo to give 0.20 parts of n-butyl O-(3-dimethylaminopropyl)salicylate.

TABLE I

Nuclear Magnetic Resonance Spectra

Example 1: Methyl O-(3-dimethylaminopropyl)salicylate: Delta 1.70–2.65(m,4H), 2.2(s,6H), 3.84(s,3H), 4.03(t,2H), 6.77–7.17(m,2H), 7.30–7.66(m,1H), 7.75–8.05(m,1H).

Example 2: Ethyl O-(2-dimethylamino-1(and 2)-methylethyl)salicylate: Delta 1.10–1.60(m,12H), 2.25–3.27(m,3H), 2.31(s,6H), 2.39(s,6H), 3.75–4.91(m,7H), 6.85–7.25(m,4H), 7.30–7.73(m,2H), 7.73–8.0(m,2H).

Example 3: Isopropyl O-(3-dimethylaminopropyl)salicylate: Delta 1.35(d,6H), 1.65–2.75(m,4H), 2.23(s,6H), 4.10(t,2H), 5.30(hep, 1H), 6.83–7.15(m,2H), 7.30–7.65(m,1H), 7.70–9.92(m,1H).

Example 5: n-Butyl O-(3-dimethylaminopropyl)salicylate: Delta 0.75–2.71(m,17H), 4.11(t,2H), 4.45(t,2H), 6.75–7.20(m,2H), 7.32–7.70(m,1H), 7.77–8.05(m,1H).

Example 6: n-Butyl O-(3-diethylaminopropyl)salicylate: Delta 0.85–1.16(m,9H), 1.17–2.20(m,6H), 2.33–2.83(m,6H), 3.95–4.43(m,4H), 6.75–7.10(m,2H), 7.25–7.60(m,1H), 7.65–7.88(m,1H).

Example 7: n-Butyl O-(2-dimethylaminoethyl)salicylate: Delta 0.77–2.0(m,7H), 2.33(s,6H), 2.80(t,2H), 4.15(t,2H), 4.28(t,2H), 6.78–7.11(m,2H), 7.27–7.60(m,1H), 7.67–7.90(m,1H).

Example 8: n-Butyl O-(2-diisopropylaminoethyl)salicylate: Delta 0.8–2.20(m,7H), 1.01(d,12H), 2.73–3.33(m,4H), 3.97(t,2H), 4.30(t,2H), 6.80–7.15(m,2H), 7.28–7.65(m,1H), 7.70–7.90(m,1H).

Example 9: n-Butyl O-(3-piperidinopropyl)salicylate: Delta 0.80–2.70(m,21H), 3.93–4.50(m,4H), 6.77–7.10(m,2H), 7.23–7.61(m,1H), 7.61–7.95(m,1H).

Example 10: n-Butyl O-(3-dimethylamino-2-methylpropyl)salicylate: Delta 0.73–2.51(m,13H), 2.21(s,6H), 3.68–4.48(m,4H), 6.78–7.13(m,2H), 7.30–7.61(m,1H), 7.70–7.91(m,1H).

Example 11: n-Butyl O-(2-morpholinoethyl)salicylate: Delta 0.78–2.0(m,7H), 2.50–3.0(m,6H), 3.60–3.83(m,4H), 4.05–4.50(m,4H), 6.80–7.15(m,2H), 7.25–7.61(m,1H), 7.65–7.95(m,1H).

Example 12: n-Butyl O-(2-piperidinoethyl)salicylate: Delta 0.77–2.0(m,13H), 2.40–3.0(m,6H), 4.03–4.45(m,4H), 6.80–7.11(m,2H), 7.25–7.60(m,1H), 7.67–7.88(m,1H).

Example 13: n-Butyl O-(2-dimethylamino-1(and 2)-methylethyl)salicylate: Delta 0.75–1.93(m,20H), 2.21–3.21(m,15H), 3.70–4.75(m,7H), 6.75–7.11(m,4H), 7.25–7.61(m,2H), 7.61–7.90(m,2H).

Example 14: n-Butyl O-[2-(hexamethyleneimine)ethyl]salicylate: Delta 0.70–2.0(m,15H), 2.58–3.17(m,6H), 4.0–4.45(m,4H), 6.78–7.13(m,2H), 7.25–7.63(m,1H), 7.67–7.97(m,1H).

Example 15: n-Butyl O-(2-dimethylaminoethyl)salicylate: Delta 1.83–2.08(m,13H), 2.45–3.20(6H, overlapping of a triplet and a quartet), 4.15(t,2H), 4.35(t,2H), 6.83–7.21(m,2H), 7.31–7.68(m,1H), 7.71–7.97(m,1H).

Example 16: iso-Amyl O-(3-dimethylaminopropyl)salicylate: Delta 0.73–1.15(6H, overlapping of two doublets), 1.15–2.67(m,7H), 2.20(s,6H), 3.90–4.50(m,4H), 6.75–7.11(m,2H), 7.21–7.58(m,1H), 7.67–7.93(m,1H).

Example 17: n-Amyl O-(3-dimethylaminopropyl)salicylate: Delta 0.73–2.70(m,13H), 2.23(s,6H), 3.97–4.45(4H, overlapping of two triplets), 6.80–7.13(m,2H), 7.27–7.65(m,1H), 7.70–7.93(m,1H).

Example 18: n-Amyl O-[2-(hexamethyleneimine)ethyl]salicylate: Delta 0.67–2.07(m,17H), 2.57–3.20(m,6H), 4.0–4.47(m,4H), 6.78–7.13(m,2H), 7.25–7.63(m,1H), 7.67–7.90(m,1H).

Example 19: n-Amyl O-(3-diethylaminopropyl)salicylate: Delta 0.70–2.20(m,17H), 2.31–2.83(m,6H), 3.93–4.43(4H, overlapping of two triplets), 6.78–7.11(m,2H), 7.27–7.63(m,1H), 7.68–7.90(m,1H).

Example 20: n-Amyl O-(3-piperidinopropyl)salicylate: Delta 0.67–2.71(m,23H), 3.93–4.50(4H, overlapping of two triplets), 6.77–7.13(m,2H), 7.23–7.63(m,1H), 7.67–7.95(m,1H).

Example 21: n-Amyl O-(2-piperidinoethyl)salicylate: Delta 0.67–2.07(m,15H), 2.28–3.0(m,6H), 3.97–4.45(q,4H), 6.75–7.11(m,2H), 7.21–7.60(m,1H), 7.63–7.89(m,1H).

Example 22: n-Amyl O-(2-morpholinoethyl)salicylate: Delta 0.67–2.10(m,9H), 2.50–3.0(m,6H), 3.61–3.83(m,6H), 4.07–4.50(4H, overlapping of two triplets), 6.80–7.15(m,2H), 7.25–7.63(m,1H), 7.67–7.90(m,1H).

Example 23: n-Amyl O-(2-diisopropylaminoethyl)salicylate: Delta 0.71–1.93(m,9H), 1.02(d,12H), 2.70–3.31(m,4H), 3.98(t,2H), 4.30(t,2H), 6.75–7.11(m,2H), 7.23–7.61(m,1H), 7.67–7.90(m,1H).

Example 24: n-Amyl O-(2-dimethylamino-1(and 2)-methylethyl)salicylate: Delta 0.67–2.07(m,18H), 2.30(s,6H), 2.37(s,6H), 2.21–3.30(m,3H), 3.70–4.78(m,7H), 6.77–7.15(m,4H), 7.25–7.61(m,2H), 7.65–7.91(m,2H).

Example 25: n-Amyl O-(3-dimethylamino-2-methylpropyl)salicylate: Delta 0.70–2.51(m,15H), 2.20(s,6H), 3.65–4.47(m,4H), 6.75–7.11(m,2H), 7.23–7.60(m,1H), 7.67–7.90(m,1H).

Example 26: n-Amyl O-(2-dimethylaminoethyl)salicylate: Delta 0.70–2.05(m,9H), 2.35(s,6H), 2.78(t,2H), 4.0–4.45(4H, overlapping of two triplets), 6.80–7.15(m,2H), 7.27–7.63(m,1H), 7.69–7.91(m,1H).

Example 27: n-Amyl O-(2-diethylaminoethyl)salicylate: Delta 0.71–2.08(m,15H), 2.65(q,4H), 2.93(t,2H), 4.13(t,2H), 4.30(t,2H), 6.78–7.17(m,2H), 7.27–7.63(m,1H), 7.68–7.93(m,1H).

Example 28: n-Hexyl O-(3-dimethylaminopropyl)salicylate: Delta 0.70–2.83(m,15H), 2.25(s,6H), 3.93–4.47(4H, overlapping of two triplets), 6.80–7.11(m,2H), 7.27–7.61(m,1H), 7.68–7.90(m,1H).

Example 29: n-Decyl O-(3-dimethylaminopropyl)salicylate: Delta 0.65–2.77(m,24H), 2.20(s,6H), 3.93–4.61(m,4H), 6.77–7.20(m,2H), 7.27–7.63(m,1H), 7.70–8.0(m,1H).

Example 30: n-Dodecyl O-(3-dimethylaminopropyl)salicylate: Delta 0.70–2.87(m,28H), 2.23(s,6H), 3.93–4.50(4H, overlapping of two triplets), 6.77–7.20(m,2H), 7.27–7.63(m,1H), 7.63–7.91(m,1H).

EXAMPLE 32

This example demonstrates the anesthetic properties of compounds of the present invention. In each case, a suitable concentration of an aqueous solution of a compound of the present invention was instilled into the conjunctival sac of the guinea pig eye, the other eye serving as an untreated control. Local anesthetic activity was tested by mechanical stimulation of the cornea. MEC is the minimal effective concentration to induce anesthesia.

Table II, below, shows the remarkable effectiveness of invention compounds in which the alkyl radical R has at least 4 carbon atoms (in particular 4 to 10 carbon atoms), and it is especially obvious from Table II that many compounds of the present invention are considerably superior to dibucaine, which at 0.1% concentration, shows anesthetic activity for only 105 minutes. For other pharmacological tests see Example 33.

TABLE II

Local anesthetic activities of compounds of the type

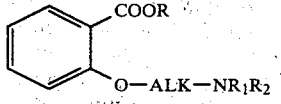

were tested. R, ALK and $NR_1R_2$, for each compound, are identified below.

| R | ALK | $NR_1R_2$ | MEC | Duration (minutes, 0.1% concentration) |
|---|---|---|---|---|
| $n\text{-}C_4H_9$ | $(CH_2)_3$ | $N(CH_3)_2$ | 0.001% | 60 |
| $iso\text{-}C_5H_{11}$ | $(CH_2)_3$ | $N(CH_3)_2$ | 0.005% | 75 |
| $n\text{-}C_5H_{11}$ | $(CH_2)_3$ | $N(CH_3)_2$ | 0.0005% | 105 |
| $n\text{-}C_6H_{13}$ | $(CH_2)_3$ | $N(CH_3)_2$ | 0.0005% | >150 |
| $n\text{-}C_{10}H_{21}$ | $(CH_2)_3$ | $N(CH_3)_2$ | 0.01% | >150 |
| $n\text{-}C_4H_9$ | $(CH_2)_3$ | piperidino | 0.001% | 105 |
| $n\text{-}C_4H_9$ | $CH_2CH(CH_3)CH_2$ | $N(CH_3)_2$ | 0.001% | 105 |
| $n\text{-}C_4H_9$ | $(CH_2)_2$ | hexamethyleneimino | 0.0005% | 120 |
| $n\text{-}C_4H_9$ | $(CH_2)_2$ | piperidino | 0.001% | 90 |
| $n\text{-}C_4H_9$ | $(CH_2)_2$ | $N(CH(CH_3)_2)_2$ | 0.00025% | 75 |
| $n\text{-}C_4H_9$ | $(CH_2)_2$ | $N(C_2H_5)_2$ | 0.001% | 105 |
| $n\text{-}C_5H_{11}$ | $(CH_2)_3$ | $N(C_2H_5)_2$ | 0.0005% | 90 |
| $n\text{-}C_5H_{11}$ | $(CH_2)_2$ | $N(C_2H_5)_2$ | 0.001% | >150 |
| $n\text{-}C_5H_{11}$ | $(CH_2)_2$ | $N(CH(CH_3)_2)_2$ | 0.0005% | 105 |
| $n\text{-}C_5H_{11}$ | $(CH_2)_2$ | $N(CH_3)_2$ | 0.0025% | 120 |
| $n\text{-}C_5H_{11}$ | $(CH_2)_2$ | hexamethyleneimino | 0.0025% | 120 |
| $n\text{-}C_5H_{11}$ | $(CH_2)_2$ | piperidino | 0.001% | >150 |
| $n\text{-}C_5H_{11}$ | $(CH_2)_3$ | piperidino | 0.001% | 135 |

TABLE III

Compounds of the type

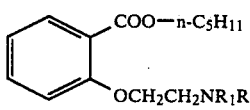

were tested. $NR_1R_2$, for each compound, is identified below.

| $NR_1R_2$ | MEC | Duration (min. 0.1% concentration) |
|---|---|---|
| morpholino | 0.01% | 60 |
| piperidino | 0.001% | >150 |
| hexamethyleneimino | 0.0025% | 120 |
| $N(CH_3)_2$ | 0.0025% | 120 |
| $N(C_2H_5)_2$ | 0.001% | >150 |
| $N(CH(CH_3)_2)_2$ | 0.0005% | 105 |

TABLE IV

Compounds of the type

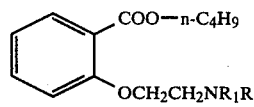

were tested, $NR_1R_2$, for each compound, is identified below.

| $NR_1R_2$ | MEC | Duration (min. 0.1% concentration) |
|---|---|---|
| morpholino | 0.05% | 5 |
| piperidino | 0.001% | 90 |
| hexamethyleneimino | 0.0005% | 120 |
| $N(CH_3)_2$ | 0.001% | 60 |
| $N(C_2H_5)_2$ | 0.001% | 105 |
| $N(CH(CH_3)_2)_2$ | 0.00025% | 75 |

The compounds of the present invention may also be administered in the form of ointments. A suitable composition would be 0.1% by weight O-Aminoalkylsalicylate in mineral oil or petrolatum.

EXAMPLE 33

The pharmacological activities of the compounds of the present invention are further exemplified by pharmacological tests of isopropyl O-(3-Dimethylaminopropyl)salicylate. This compound showed no toxicity when administered orally in dosages of 300 mg/kg to mice. When tested in vitro on guinea pig ileum at a screen dose of 10 μg/ml this compound showed a significant antiserotonin activity and moderate antihistaminic and anticholinergic activities.

We claim:

1. A compound of the formula

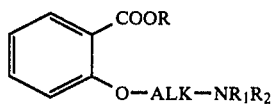

I wherein R is $C_4$–$C_{14}$ alkyl, ALK is a lower alkylene radical, $R_1$ and $R_2$ are the same or different and are hydrogen or lower alkyl, $R_1$ and $R_2$ taken together form a 5–7 atom ring which includes 1–2 nitrogen atoms, the other ring members being carbon atoms, and the pharmaceutically acceptable acid addition salts thereof.

2. n-Hexyl O-(3-dimethylaminopropyl)salicylate and the pharmaceutically acceptable acid addition salts thereof, according to claim 1.

3. n-Heptyl O-(3-dimethylaminopropyl)salicylate and the pharmaceutically acceptable acid addition salts thereof, according to claim 1.

4. n-Octyl O-(3-dimethylaminopropyl)salicylate and the pharmaceutically acceptable acid addition salts thereof, according to claim 1.

5. n-Nonyl O-(3-dimethylaminopropyl)salicylate and the pharmaceutically acceptable acid addition salts thereof, according to claim 1.

6. n-Decyl O-(3-dimethylaminopropyl)salicylate and the pharmaceutically acceptable acid addition salts thereof, according to claim 1.

7. A method for topical local anesthesia which comprises administering topically an effective amount of a compound or acid addition salt as defined in any one of claims 1 to 6 in the presence of an inert carrier.

8. A topical local anesthetic pharmaceutical composition comprising an effective amount of a compound or an addition salt as defined in any one of claims 1 to 6 and a pharmaceutically acceptable carrier.

* * * * *